(12) United States Patent
Bauer et al.

(10) Patent No.: US 10,269,464 B2
(45) Date of Patent: Apr. 23, 2019

(54) ISOTOPE TAGGING FOR WORKPIECE AUTHENTICATION

(71) Applicant: Board of Trustees of Michigan State University, East Lansing, MI (US)

(72) Inventors: Wolfgang Bauer, East Lansing, MI (US); Bradley Sherrill, Okemos, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 331 days.

(21) Appl. No.: 15/197,940

(22) Filed: Jun. 30, 2016

(65) Prior Publication Data

US 2017/0125213 A1    May 4, 2017

Related U.S. Application Data

(60) Provisional application No. 62/250,609, filed on Nov. 4, 2015.

(51) Int. Cl.
| | | |
|---|---|---|
| *G21H 5/02* | (2006.01) | |
| *G09F 3/00* | (2006.01) | |
| *H04W 12/00* | (2009.01) | |
| *B42D 25/405* | (2014.01) | |
| *G21G 1/00* | (2006.01) | |
| *G21G 1/10* | (2006.01) | |

(52) U.S. Cl.
CPC ............. *G21H 5/02* (2013.01); *B42D 25/405* (2014.10); *G09F 3/00* (2013.01); *H04W 12/00* (2013.01); *G01N 2458/15* (2013.01); *G21G 1/0005* (2013.01); *G21G 1/10* (2013.01); *H01J 2237/31711* (2013.01); *H05H 2277/12* (2013.01); *Y10T 428/24802* (2015.01)

(58) Field of Classification Search
CPC ..... G21H 5/02; G21G 1/04; Y10T 428/24802
See application file for complete search history.

(56) References Cited

U.S. PATENT DOCUMENTS

| | | |
|---|---|---|
| 5,177,360 A | 1/1993 | Fernandez-Rubio |
| 6,106,021 A | 8/2000 | Phillips |
| 6,616,964 B1 | 9/2003 | Hampp et al. |
| 6,740,875 B1 | 5/2004 | Ishikawa et al. |
| 8,864,038 B2 | 10/2014 | Marka et al. |
| 8,931,696 B2 | 1/2015 | Hood |
| 2009/0162278 A1* | 6/2009 | Ravn ............... G21G 1/001 424/1.37 |

OTHER PUBLICATIONS

"Experimental Equipment Needs for the Facility for Rare Isotope Beams (FRIB)," prepared for the APS DNP Low Energy Town Meeting, published Feb. 13, 2015, pp. 1-30.

(Continued)

*Primary Examiner* — Gerard Higgins
(74) *Attorney, Agent, or Firm* — Harness, Dickey & Pierce, PLC

(57) ABSTRACT

A method of assisting with authenticating a workpiece is provided. In another aspect, ions are generated, accelerated in an accelerator, an isotope is created, and then the isotope is implanted within a workpiece to assist with authenticating of the workpiece. A further aspect includes a workpiece substrate, a visual marker and an isotope internally located within the substrate adjacent the visual marker.

20 Claims, 5 Drawing Sheets

(56) References Cited

OTHER PUBLICATIONS

Hausmann, M., et al.; "Design of the Advanced Rare Isotope Separator ARIS at FRIB," Nuclear Instruments and Methods in Physics Research B, 317, 2013, pp. 349-353.
"Isotope-Ratio Mass Spectrometry," Wikipedia, modified Sep. 16, 2015, printed Nov. 2, 2015, 11 pages.
Mashberg, Tom; "Art Forgers Beware: DNA Could Thwart Fakes," The New York Times, Oct. 12, 2015, four pages.
Nuclear Physics News International, vol. 24, Issue 1, Jan.-Mar. 2014, pp. 1-40.
Schriber, Stan O. et al., "Rare-Isotope (Heavy Ion) Accelerators," Proc. of 11th Workshop on RF Superconductivity, (2003), 6 pages.

\* cited by examiner

Beam

| | | |
|---|---|---|
| AZ | 156Dy | |
| Energy | 228.3 | MeV/u |

Fragment

| | | |
|---|---|---|
| Energy | 180 | MeV/u |
| $B_p$ (Q=Z) | 4.678 | Tm |
| Fast beam rate | 9.37e+9 | pps |
| Stopped beam rate | 7.50e+7 | pps |
| Reaccelerated beam rate | 2.10e+7 | pps |

Beam

| | | |
|---|---|---|
| AZ | 198Pt | |
| Energy | 210.1 | MeV/u |

Fragment

| | | |
|---|---|---|
| Energy | 165.3 | MeV/u |
| $B_p$ (Q=Z) | 4.930 | |
| Fast beam rate | 2.50e+8 | pps |
| Stopped beam rate | 6.32e+6 | pps |
| Reaccelerated beam rate | 1.42e+6 | pps |

Beam

| | | |
|---|---|---|
| AZ | 64Ni | |
| Energy | 253 | MeV/u |

Fragment

| | | |
|---|---|---|
| Energy | 204.9 | MeV/u |
| $B_p$ (Q=Z) | 5.011 | Tm |
| Fast beam rate | 4.29e+10 | pps |
| Stopped beam rate | 3.44e+8 | pps |
| Reaccelerated beam rate | 9.62e+7 | pps |

| Beam | | |
|---|---|---|
| AZ | 130Te | |
| Energy | 216.8 | MeV/u |
| Fragment | | |
| Energy | 173.9 | MeV/u |
| $B_p$ (Q=Z) | 5.003 | Tm |
| Fast beam rate | 1.62e+9 | pps |
| Stopped beam rate | 1.29e+7 | pps |
| Reaccelerated beam rate | 3.62e+6 | pps |

| Beam | | |
|---|---|---|
| AZ | 238U | |
| Energy | 203 | MeV/u |
| Fragment | | |
| Energy | 158.8 | MeV/u |
| $B_p$ (Q=Z) | 4.897 | |
| Fast beam rate | 1.66e+7 | pps |
| Stopped beam rate | 3.21e+6 | pps |
| Reaccelerated beam rate | 7.19e+5 | pps |

ISOTOPE TAGGING FOR WORKPIECE AUTHENTICATION

CROSS REFERENCE TO RELATED APPLICATIONS

This application claims the benefit of U.S. Provisional Application No. 62/250,609, filed on Nov. 4, 2015, the entire disclosure of which is incorporated by reference herein.

BACKGROUND AND SUMMARY

The present invention relates generally to isotope tagging and more particularly to isotope tagging for workpiece authentication.

Artwork forgeries have always posed a problem. Recently, some have theorized that synthetic DNA tagging of paintings or sculptures could possibly provide authentication for artists. This DNA concept, however, may still be prone to copying or altering by sophisticated forgers with scientific knowledge.

Others have attempted to use chemical or isotope markers. Such conventional constructions are disclosed in: U.S. Pat. No. 8,931,696 entitled "Counterfeit Detection System and Method" which issued to Hood on Jan. 13, 2015; U.S. Pat. No. 8,864,038 entitled "Systems and Methods for Fraud Prevention, Supply Chain Tracking, Secure Material Tracing and Information Encoding using Isotopes and Other Markers" which issued to Marka et al. on Oct. 21, 2014; and U.S. Pat. No. 5,177,360 entitled "Devices and Method to Confirm the Authenticity of Art Objects" which issued to Fernandez-Rubio on Jan. 5, 1993. These prior methods, however, use relatively inexpensive and common isotopes which can be easily obtained by a sophisticated forger with access to common medical laboratories. For example, the Hood patent mixes a liquid form of the marker with paint applied to a canvas or a dye applied to a textile, or weaves a solid form of the marker into clothing. The Marka patent pelletizes the marker for placement into bulk manufactured items. The Fernandez-Rubio patent pipetts the marker into a sealed metal enclosed cavity which is adhered to an art object. Accordingly, these conventional methods are not well suited to prevent sophisticated forgeries of unique, one-of-a-kind items.

In accordance with the present invention, a method of assisting with authenticating a workpiece is provided. In another aspect, ions are generated, accelerated in an accelerator (for example, a cyclotron), an isotope is created, and then the isotope is implanted within a workpiece to assist with authenticating of the workpiece. A further aspect includes a workpiece substrate, a visual marker and an isotope internally located within the substrate adjacent the visual marker. Another aspect employs one or more isotopes having a half-life of at least three months, a precise and measurable alpha and/or gamma decay emission, and a unique isotope signature. In still another aspect, a system includes a heavy ion source, a cyclotron accelerator, an isotope separator, an optional cryogenic gas stopper, an optional fragmented isotope reaccelerator, and a rare isotope tagging station for tagging a high value workpiece with the rare isotope. Yet a further aspect uses a unique isotope, a pattern of one or more isotopes, and/or a combination of isotopes, to tag a high value workpiece for later authentication.

The present method, workpiece and system are advantageous over conventional approaches. For example, rare and expensive to produce isotopes are employed which can only be created and implanted in the workpiece in a few expensive facilities, which is well beyond the financial means and technical knowledge of forgers. Furthermore, the present method, workpiece and system allow for extremely accurate and unique authentication and identification tagging or marking. Moreover, the present isotope tagging has a long and predictable lifetime, a precise and measurable decay signature, a unique decay signature, is nonhazardous to people, and will not harm the workpiece. The present method, workpiece and system have the rare isotope implanted within the workpiece after the workpiece is created. Advantageously, the present system implants small quantities of rare isotopes into a workpiece and these isotopes can only be produced by extremely expensive equipment, which are not accessible to forgers. Additionally, the authentication via detection of the decay signatures of the implanted rare ions can be performed completely nondestructively via portable gamma ray detectors with sufficient energy resolution. Additional advantages and features of the present invention will be apparent from the following description and appended drawings.

BRIEF DESCRIPTION OF THE DRAWINGS

FIG. 4B is a table showing values associated with isotope $_{64}^{148}Gd$ of FIG. 4A;

FIG. 4C is a table showing values associated with isotope $_{76}^{194}Os$ of FIG. 4A;

FIG. 4D is a table showing values associated with isotope $_{26}^{60}Fe$ of FIG. 4A;

FIG. 4E is a table showing values associated with isotope $_{50}^{126}Sn$ of FIG. 4A; and FIG. 4F is a table showing values associated with isotope $_{88}^{228}Ra$ of FIG. 4A.

DETAILED DESCRIPTION

Figure 1:
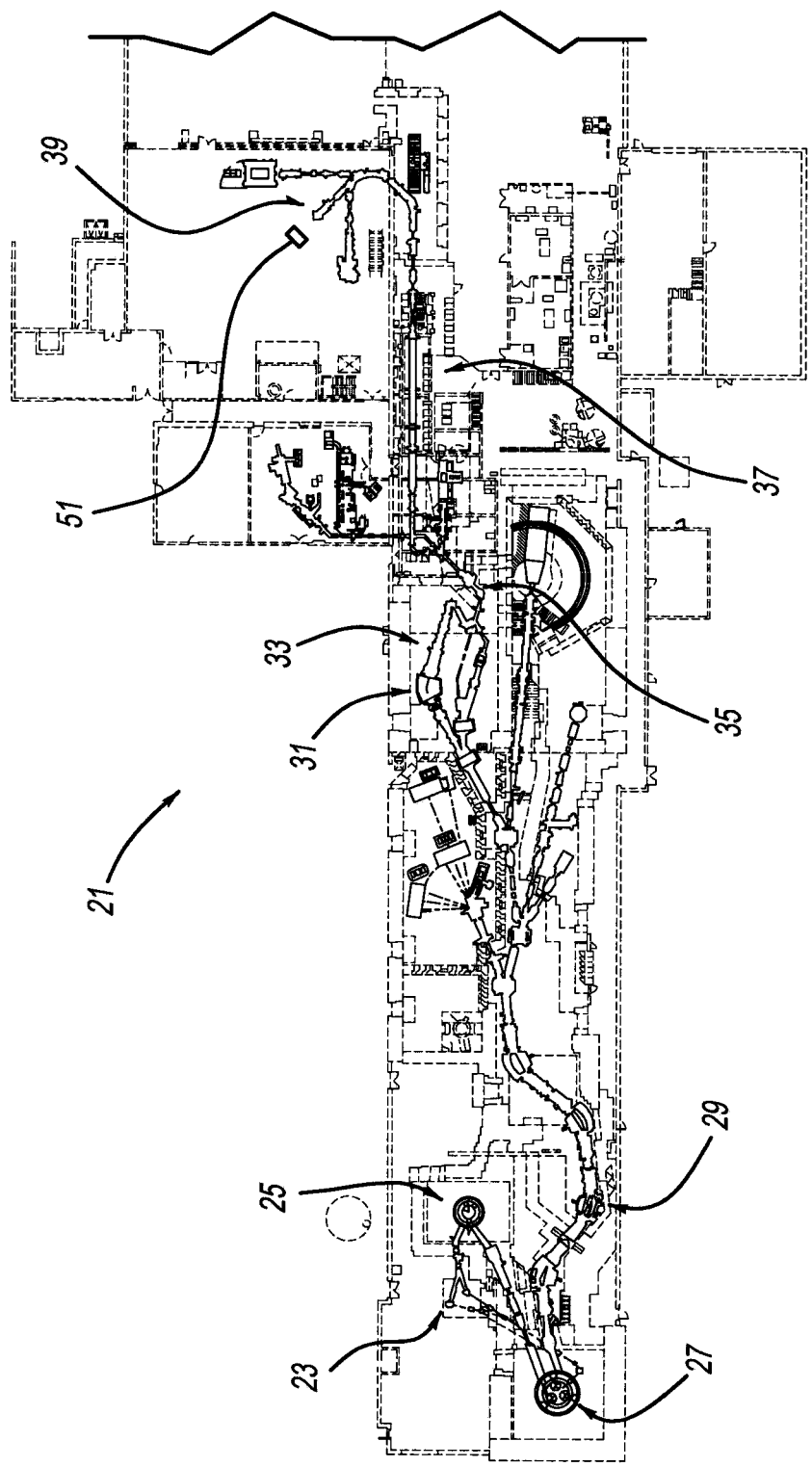
FIG. 1 is a diagrammatic view showing superconducting cyclotron equipment used with the present method and system.
Figure 2:
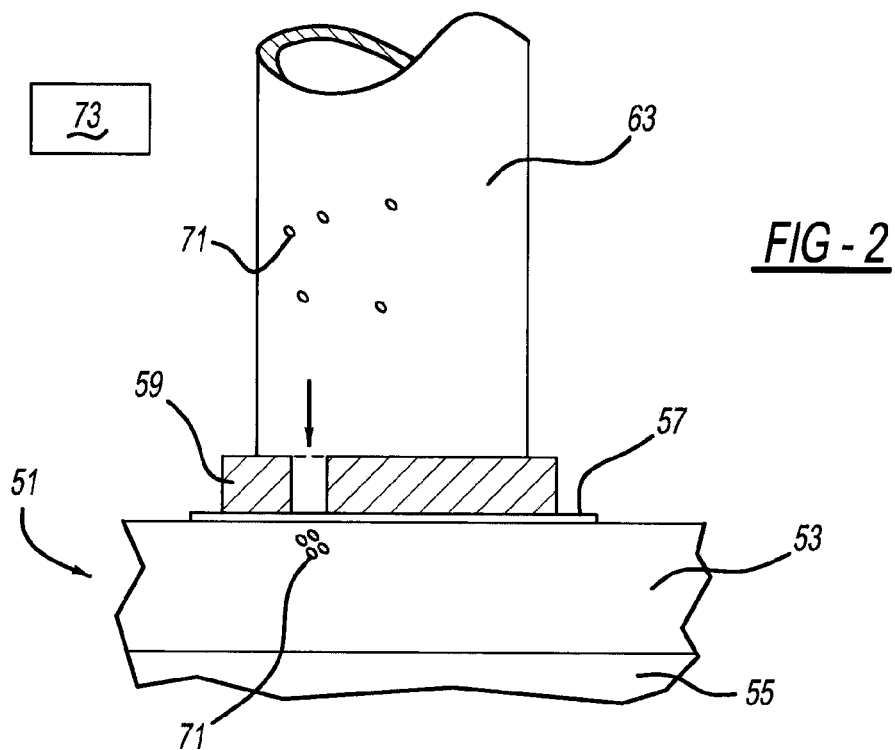
FIG. 2 is an enlarged side elevational view showing the present system including isotopes implanted within a workpiece.
Figure 3:
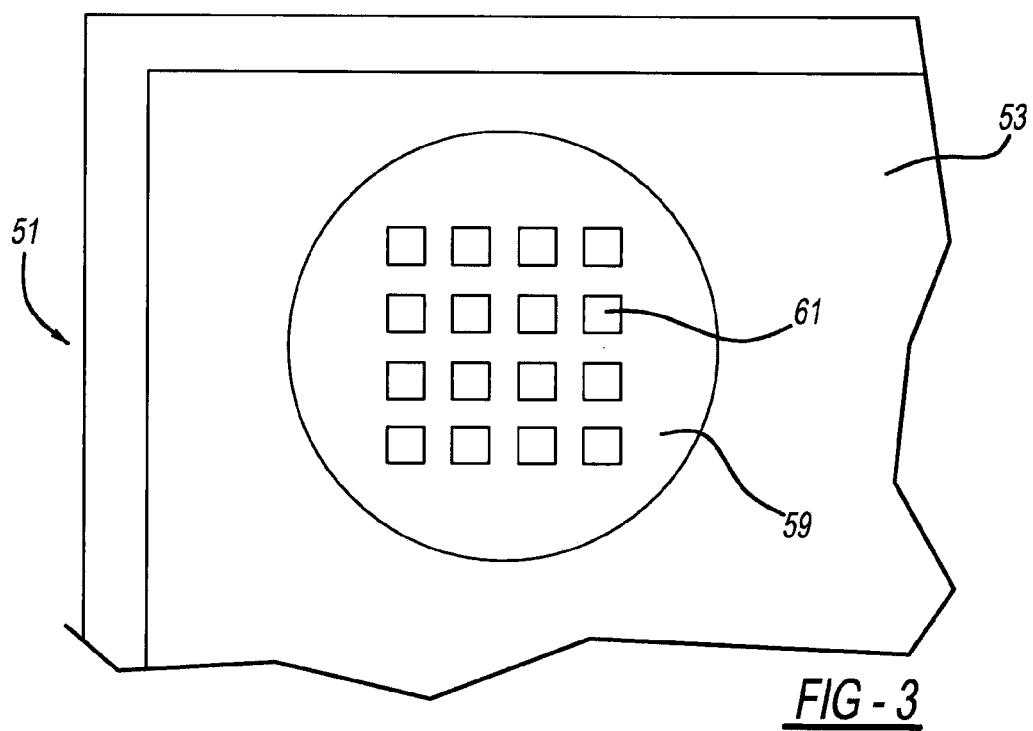
FIG. 3 is an enlarged back elevational view showing the present system including a visual marker and/or mask located on the workpiece.
Figure 4A:
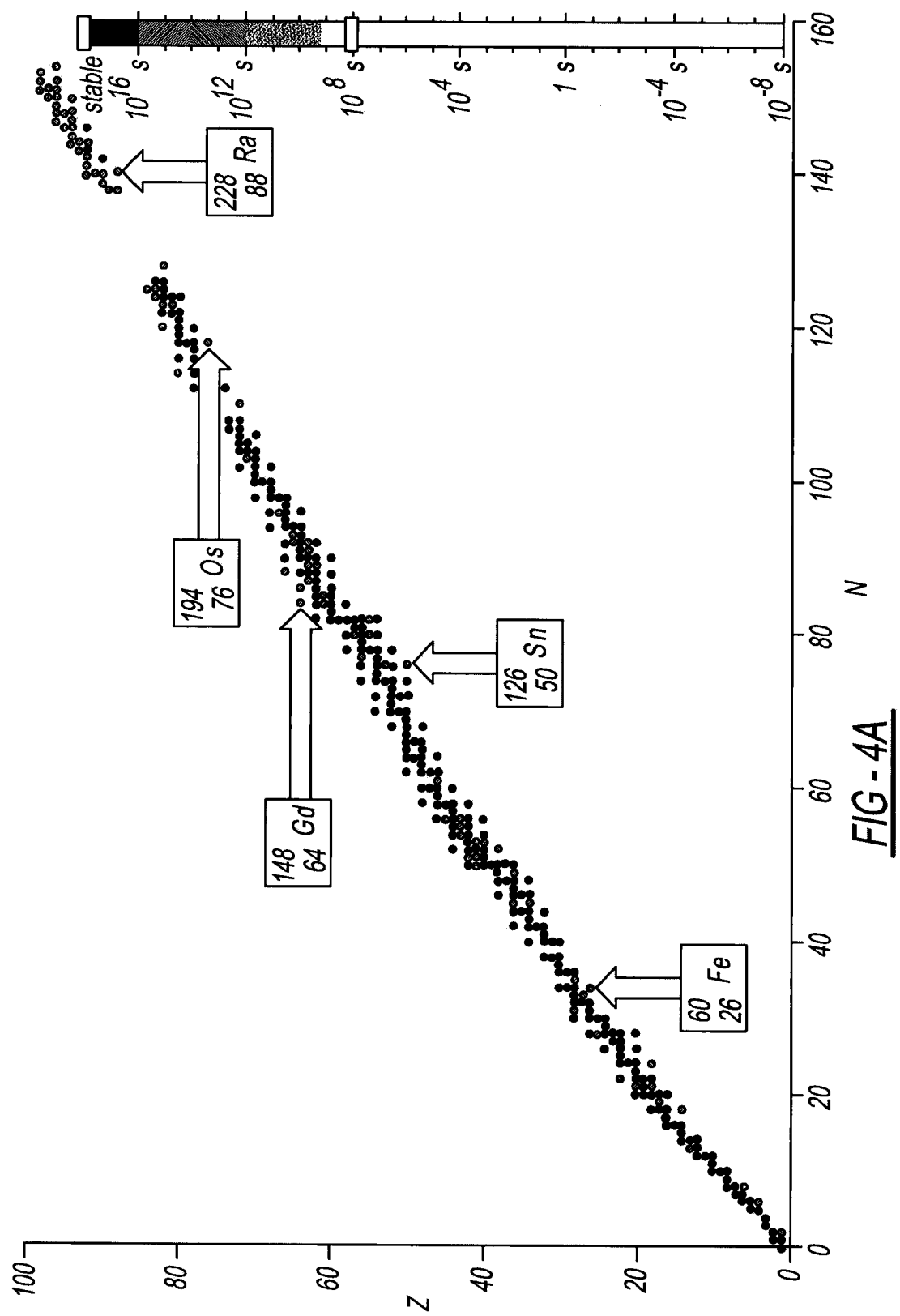
FIG. 4A is a graph showing predicted rare isotope charge versus isotope neutron number rates expected after completion of the Facility for Rare Isotope Beams.

The present method, workpiece and system are shown in FIGS. 1-3. A superconducting cyclotron facility 21 includes an ion source 23, a K500 cyclotron 25, a K1200 cyclotron 27, an A1900 fragment separator 29, a momentum compression ANL gas catcher 31, an optional cryogenic gas stopper 33, a low energy beam line EBIT cooler buncher helium jet 35, an optional linear reaccelerator 37, and an isotope tagging station 39. The preceding items are all computer controlled. Ion source 23 includes an electron cyclotron resonance ("ECR") source or an electron beam ion source ("EBIS"), such a using an ion gun employing microwaves in a low pressure gas or thermionic emissions of electrons to ionize the base material in its gaseous state. Superconducting cyclotron facility 21 is of the type disclosed in Hausmann, M., et al., "Design of the Advanced Rare Isotope Separator ARIS at FRIB," Nucl. Instr. Meth. B 317 (Jul. 4, 2013) 349-353; and "Experimental Equipment Needs for the Facility for Rare Isotope Beams (FRIB)—whitepaper" (Feb.

13, 2015). Facility 21 uses projectile fragmentation and induced in-flight fission of heavy-ion primary beams at energies of 100 MeV and preferably at least 200 MeV/u and at a beam power of at least 1 kW and preferably at least 400 kW, to generate rare isotope beams. More particularly, reaccelerator 37 is a superconducting—RF driver, linear accelerator. Fragment separator 29 is preferably a three-stage fragment separator including a first stage vertically bending preseparator followed by two horizontally-bending second and third stages using multiple superferric magnet dipoles and quadruples to focus the beam and/or correct image aberrations. FIG. 1 illustrates the equipment layout of the National Superconducting Cyclotron Laboratory with the proposed location of the isotope tagging station within the accelerator complex, but alternate layouts may be employed.

A high value workpiece 51 is an original artwork, such as a painting, print, photograph, sculpture, vase, tapestry, document or the like. Alternately, workpiece is an antique, jewelry, watch, vintage automobile component such as an engine block, or other such expensive or one-of-a-kind object that is prone to having forgeries or false reproductions made thereof. In the painting workpiece 51 example used herewith, a substrate 53 is canvas with an aesthetic painted layer 55 on a front surface. If a sculpture, substrate 53 includes the clay or ceramic material. If jewelry or an automobile component, substrate 53 may be a metal structure.

First, a visual marker 57 is placed in a small area on a backside of workpiece 51, such as by printing, painting or any other manner which will last for decades without significant degradation or harm to aesthetic painted layer 55. Marker 57 provides a visual point for the authenticator to begin seeking the isotope tag. One or more metallic masks 59 are temporarily placed against marker 57. Each mask 59 is a lead plate of about 2-10 mm thick with one or more holes 61 therethrough. Workpiece 51 is then placed in a fixture within isotope tagging station 39. A hollow and elongated beam pipe 63 is sealed against mask 59.

A beam of heavy ions is generated from source 23 and accelerated to approximately half the speed of light by cyclotrons 25 and 27. Nuclear reactions occur at the beginning of the fragment separator 29 to create the desired isotope. The desired isotope 71 is selected by the fragment separator and then transported for use in a beam pipe or optionally travel through catcher 31 and are slowed down in helium gas stopper 33. Optionally, isotopes 71 are thereafter re-accelerated in linear accelerator 37 to create a precise workpiece-penetration speed. Isotopes from the fragment separator or optionally reaccelerated isotopes 71 then travel through pipe 63 and those isotopes aligned with holes 61 in mask 59, penetrate into and are implanted between 5 mm and 1 micron deep, and more preferably at or between 1 mm and 10 microns inside workpiece 51 relative to the backside surface thereof adjacent pipe 63.

Multiple masks 59 with different hole quantities or patterns (as shown in FIG. 3) may be employed to provide unique or customized identifiers. Moreover, different combinations of rare isotopes 71 may be implanted through a single or different combinations of mask holes 61 to provide unique or customized identifiers. In the example shown in FIG. 3, at least four and more preferably sixteen different isotope locations are provided for a single workpiece. The identifier may be published in a reference guide for each original workpiece. Since a rare isotope is chosen that can only be implanted in expensive accelerator facilities (i.e., >$500 million (2015 USD)), the present approach is too expensive and technically difficult for a forger. However, the present approach is feasible for a physicist with legitimate access to such a system. The authenticator uses a gamma ray detector 73 with keV energy resolution or the like to identify the type of isotope and position of the isotope in a nondestructive manner, to assist in authentication (which includes identification) of the workpiece.

Referring to FIGS. 4A-4F, desired rare isotopes are those that are accelerated with an energy of at least 100 A-MeV and with a beam power of at least 1 kW. Furthermore, the desired rare isotopes have a half-life decay rate of at least three months, have a measurable and precise alpha or gamma decay emission (but not a beta decay emission), and have a unique and repeatable isotope signature which cannot be imitated by other isotopes. Nonlimiting exemplary desired isotopes include $_{64}^{148}$Gd, $_{76}^{194}$Os, $_{26}^{60}$Fe, $_{50}^{126}$Sn, $_{88}^{228}$Ra, $_{82}^{210}$Pb, and the like. Other such rare isotopes may be employed beyond those specifically identified. However, $_{14}^{32}$Si, for example, is not desired since it is a pure beta emitter which makes it difficult to identify the specific isotope due to a lack of unique energies.

While various embodiments have been disclosed, other embodiments may fall within the scope of the present invention. For example, the mask can have alternate external and/or hole shapes, such as elongated slots of straight or curved shapes. Additional or alternate accelerator, separator, catcher, stopper and jet equipment may be used as long as the facility is not commonly available and can produce rare isotopes accelerated with the above-specified energies and beam powers; such alternate equipment may lead to difference rates of isotope production as compared to FIGS. 4B-4F discussed hereinabove. Additional modifications can be made which fall within the scope and spirit of the present invention.

The invention claimed is:

1. A method of assisting with authenticating a workpiece, the method comprising:
   (a) generating ions;
   (b) accelerating the ions in an accelerator with an energy of at least 100 A-MeV and a beam power of at least 1 kW;
   (c) creating an accelerated isotope from the accelerated ions; and
   (d) implanting the accelerated isotope in the workpiece to assist with the authenticating of the workpiece.

2. The method of claim 1, wherein the accelerating of the ions occurs by using a facility comprising a superconducting cyclotron accelerator.

3. The method of claim 2, wherein the generating of the ions occurs by using one of: (a) an electron cyclotron resonance source or (b) an electron beam ion source.

4. The method of claim 2, wherein the generating of the ions occurs by using one of: (a) microwaves in a low pressure gas, or (b) thermionic emissions of electrons to ionize a base material in its gaseous state.

5. The method of claim 2, wherein the ions are rare heavy ions.

6. The method of claim 1, further comprising using a gamma ray detector with keV energy resolution to nondestructively identify at least one of: (a) the isotope, or (b) a position of the isotope, to assist in the authenticity of the workpiece after the implanting step.

7. The method of claim 1, further comprising placing a removable mask, having a unique hole pattern, against the workpiece and emitting the accelerated isotope through the hole pattern before the implanting step.

8. The method of claim 1, further comprising using different combinations of rare isotopes to create customizable workpiece identifiers in additional workpieces.

9. The method of claim 1, further comprising applying a visual marker to the workpiece adjacent to a location of the isotope implantation.

10. The method of claim 1, wherein the creating of the accelerated isotope comprises fragmenting the accelerated ions to create a fragmented isotope and then re-accelerating the fragmented isotope.

11. The method of claim 1, wherein the workpiece includes a painting on canvas and the isotope penetrates into and is implanted inside the workpiece between 5 mm and 1 micron deep from an entry surface thereof.

12. The method of claim 1, wherein the workpiece is metallic and the isotope penetrates into and is implanted inside the workpiece between 5 mm and 1 micron deep from an entry surface thereof.

13. A method of assisting with authenticating workpieces, the method comprising:
(a) generating ions;
(b) accelerating the ions in a superconducting cyclotron accelerator;
(c) creating a first combination of rare isotopes and a second combination of rare isotopes;
(d) transmitting the first combination of rare isotopes through holes in at least one removable mask toward a first of the workpieces;
(e) transmitting the second combination of rare isotopes through the holes in the at least one removable mask toward a second of the workpieces; and
(f) causing the first and second combinations of rare isotopes to penetrate into the respective workpieces between 5 mm and 1 micron deep from an entry surface of each of the workpieces adjacent the mask, wherein the first and second combinations of rare isotopes are different, which creates unique authenticating indications.

14. The method of claim 13, wherein each of the rare isotopes has a measurable and precise alpha or gamma decay emission, but not a beta decay emission.

15. The method of claim 13, wherein the generating of the ions occurs by using one of: (a) an electron cyclotron resonance source or (b) an electron beam ion source.

16. The method of claim 13, wherein the generating of the ions occurs by using one of: (a) microwaves in a low pressure gas, or (b) thermionic emissions of electrons to ionize a base material in its gaseous state.

17. The method of claim 13, further comprising using an isotope ratio mass spectrometer to nondestructively identify at least one of: (a) the first or second combinations of rare isotopes, or (b) a position of the first or second combinations of rare isotopes, to assist in the authenticity of the workpieces after the implanting step.

18. The method of claim 13, further comprising applying a visual marker to each of the workpieces adjacent to a location of implantation of the first or second combinations of rare isotopes.

19. A workpiece comprising:
(a) a pre-made workpiece substrate;
(b) a visual marker; and
(c) rare isotopes internally located within the pre-made substrate adjacent the visual marker, the rare isotopes providing a customized identifier based on at least one of: a pattern, quantity, isotope combinations, or half-life;
(d) the rare isotopes having:
the half-life of at least three months;
a precise and measurable alpha or gamma decay emission;
a unique isotope signature; and wherein the rare isotopes are a combination of rare isotopes including at least one of: $^{148}_{64}Gd$, $^{194}_{76}Os$, $^{60}_{26}Fe$, $^{126}_{50}Sn$, $^{228}_{88}Ra$, or $^{210}_{82}Pb$.

20. The workpiece of claim 19, wherein:
the combination of the rare isotopes is arranged in a unique pattern implanted within the substrate between 5 mm and 1 micron deep from an entry surface thereof.

* * * * *